United States Patent
Boss et al.

(10) Patent No.: US 9,470,671 B1
(45) Date of Patent: Oct. 18, 2016

(54) DETECTION OF TRACE AMOUNTS OF PERCHLORATE USING SERS-ACTIVE CAPTURE MATRICES

(71) Applicant: The United States of America as represented by the Secretary of the Navy, Washington, DC (US)

(72) Inventors: Pamela A. Boss, San Diego, CA (US); Michael D. Putnam, San Diego, CA (US)

(73) Assignee: The United States of America as represented by Secretary of the Navy, Washington, DC (US)

( * ) Notice: Subject to any disclaimer, the term of this patent is extended or adjusted under 35 U.S.C. 154(b) by 0 days.

(21) Appl. No.: 14/719,114

(22) Filed: May 21, 2015

(51) Int. Cl.
*G01N 33/18* (2006.01)
*G01N 21/65* (2006.01)
*B01J 19/00* (2006.01)
*G01N 27/333* (2006.01)

(52) U.S. Cl.
CPC .......... *G01N 33/182* (2013.01); *G01N 21/658* (2013.01); *G01N 27/333* (2013.01); *G01N 2021/651* (2013.01)

(58) Field of Classification Search
CPC .................. Y10T 436/20; Y10T 436/200833; G01N 33/182; G01N 33/18; G01N 33/00; G01N 21/658; G01N 21/65; G01N 21/63; G01N 21/62; G01N 27/333; G01N 27/30; G01N 27/28; G01N 27/26
USPC ............................ 436/125, 124; 422/68.1, 50
See application file for complete search history.

(56) References Cited

U.S. PATENT DOCUMENTS

| | | | |
|---|---|---|---|
| 6,614,523 B1 * | 9/2003 | Boss ...................... | B82Y 15/00 356/301 |
| 7,116,416 B1 * | 10/2006 | Boss ...................... | B82Y 15/00 356/301 |
| 7,879,625 B1 * | 2/2011 | Boss ...................... | B82Y 25/00 427/2.11 |

OTHER PUBLICATIONS

Gu et al, Final Report: Development of a Portable Surface Enhanced Raman Sensor for Real-Time Detection and Monitoring of Perchlorate and Energetics, SERDP Project ER-1602, SERDP, Jan. 2012, pp. 1-79.*

Putnam et al, The Evaluation of Two Commercially Available Portable Raman Systems, Analytical Chemistry Insights, vol. 8, 2013, pp. 83-97.*

SERDP, Development of a Surface-Enhanced Raman Spectroscopy (SERS)-based Sensor for the Long Term Monitoring of Toxic Anions, Strategic Environmental Research and Development Program, Space and Naval Warfare Systems Center, San Diego , CA, Jun. 2003, p. 1-166.*

Boss, The Use of Conventional and Surface Enhanced Raman Spectroscopy to Evaluate Chemistries for the Detection and/or Remediation of Perchlorate in Aqueous Systems, American Chemical Society, 2011, pp. 77-89.*

P.A. Mosier-Boss et al.; Detection of Anions by Normal Raman Spectroscopy and Surface-Enhanced Raman Spectroscopy of Cationic-Coated Substrates; Appl. Spectrosc., vol. 57, 99. 1129-1137 (2003).

B. Gu et al.; Perchlorate Detection at Nanomolar Concentrations by Surface-Enhanced Raman Scattering, Appl. Spectrosc., vol. 63, pp. 98-102 (2009).

P.A. Mosier-Boss et al.; Surface-Enhanced Raman Spectroscopy Substrate Composed of Chemically Modified Gold Colloid Particles Immobilized on Magnetic Microparticles; Anal. Chem., vol. 77, pp. 1031-1037 (2005).

P.A. Mosier-Boss et al.; Detection of perchlorate using Ag/DMAH+ SERS-active capture matrices; Spectrochimica Acta Part A: Molecular and Biomolecular Spectroscopy 133 pp. 156-164 (May 28, 2014).

* cited by examiner

*Primary Examiner* — Christine T Mui
(74) *Attorney, Agent, or Firm* — SPAWAR Systems Center Pacific; Kyle Eppele; J. Eric Anderson

(57) ABSTRACT

A perchlorate detector comprising: surface-enhanced Raman spectroscopy (SERS)-active, magnetic, capture matrices that are selective for perchlorate, wherein the capture matrices are designed to be added to a sample solution; a detection chamber configured to hold the sample solution and the capture matrices; a selectively engageable magnet assembly coupled to the detection chamber such that when the magnet assembly is engaged or disengaged the capture matrices are respectively confined or not confined to a confinement region of the detection chamber; and a Raman spectrometer optically aligned with the confinement region of the detection chamber and configured to interrogate the capture matrices when the magnet assembly is engaged in order to detect and determine a concentration of perchlorate bound to the capture matrices.

18 Claims, 10 Drawing Sheets

US 9,470,671 B1

DETECTION OF TRACE AMOUNTS OF PERCHLORATE USING SERS-ACTIVE CAPTURE MATRICES

FEDERALLY-SPONSORED RESEARCH AND DEVELOPMENT

The United States Government has ownership rights in this invention. Licensing and technical inquiries may be directed to the Office of Research and Technical Applications, Space and Naval Warfare Systems Center, Pacific, Code 72120, San Diego, Calif., 92152; voice (619) 553-5118; ssc_pac_t2@navy.mil. Reference Navy Case Number 103038.

BACKGROUND OF THE INVENTION

The invention described herein relates to the field of detecting perchlorate. Perchlorate has been used as the oxidizer component and primary ingredient in solid propellant for rockets and missiles. Recently it was shown that perchlorate is present in several fertilizers and fertilizer components at levels up to 0.84 wt %, suggesting that fertilizers could be a source for perchlorate accumulation in the food chain. Perchlorate is exceedingly mobile in aqueous systems and can persist for many decades under typical ground- and surface-water conditions. It has been found in groundwater, drinking water, and soils, mainly in the southwestern United States, at levels ranging from 8 to 3700 ppb. Perchlorate affects the thyroid gland by blocking iodine uptake resulting in lower thyroid hormone levels. There is a need for an improved perchlorate detector.

SUMMARY

Disclosed herein is a perchlorate detector comprising: surface-enhanced Raman spectroscopy (SERS)-active, magnetic, capture matrices, a detection chamber, a selectively engageable magnet assembly, and a Raman spectrometer. The capture matrices are selective for perchlorate and are designed to be added to a sample solution. The detection chamber is configured to hold the sample solution and the capture matrices. The selectively engageable magnet assembly is coupled to the detection chamber such that when the magnet assembly is engaged or disengaged the capture matrices are respectively confined or not confined to a confinement region of the detection chamber. The Raman spectrometer is optically aligned with the confinement region of the detection chamber and configured to interrogate the capture matrices when the magnet assembly is engaged in order to detect and determine a concentration of perchlorate bound to the capture matrices.

The invention disclosed herein may also be described as a perchlorate detection method. The first step of the method provides for mixing a sample solution with surface-enhanced Raman spectroscopy (SERS)-active, magnetic, capture matrices that are selective for perchlorate to create a mixed suspension. The next step provides for containing the mixed suspension in a detection chamber. The next step provides for engaging a magnet assembly to confine the capture matrices to a confinement region of the detection chamber. The next step provides for interrogating the capture matrices confined to the confinement region with a Raman spectrometer that is optically aligned with the confinement region in order to detect and determine a concentration of perchlorate bound to the capture matrices.

BRIEF DESCRIPTION OF THE DRAWINGS

Throughout the several views, like elements are referenced using like references. The elements in the figures are not drawn to scale and some dimensions are exaggerated for clarity.

DETAILED DESCRIPTION OF EMBODIMENTS

The disclosed methods and systems below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

Figure 1A:
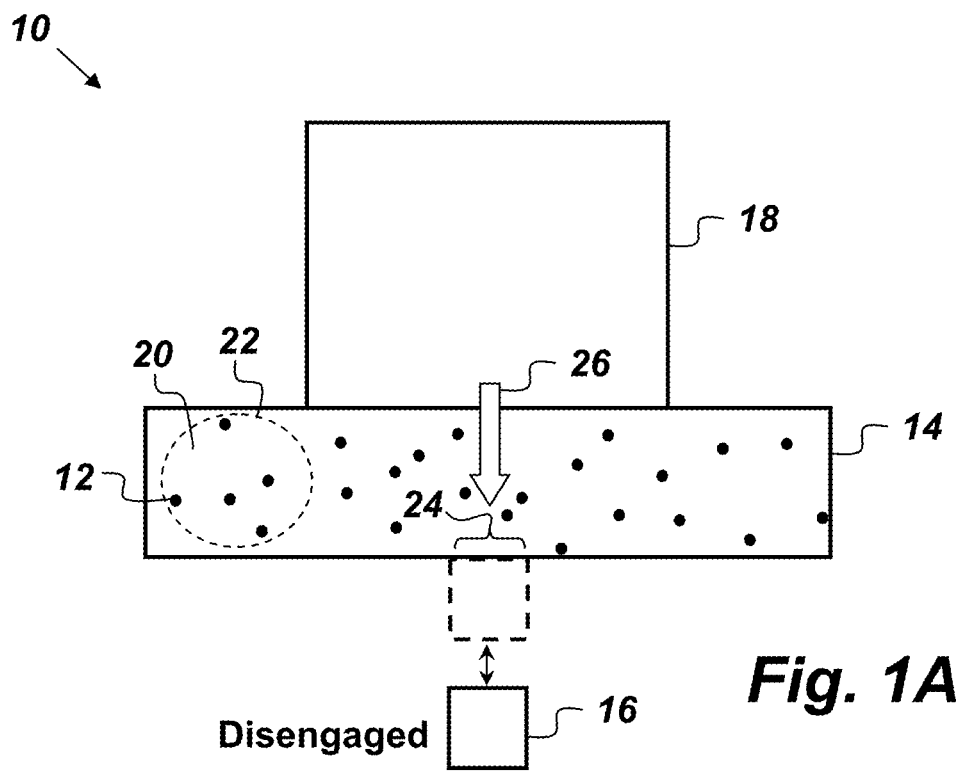
FIGS. 1A and 1B are illustrations of embodiments of a perchlorate detector.
Figure 1B:
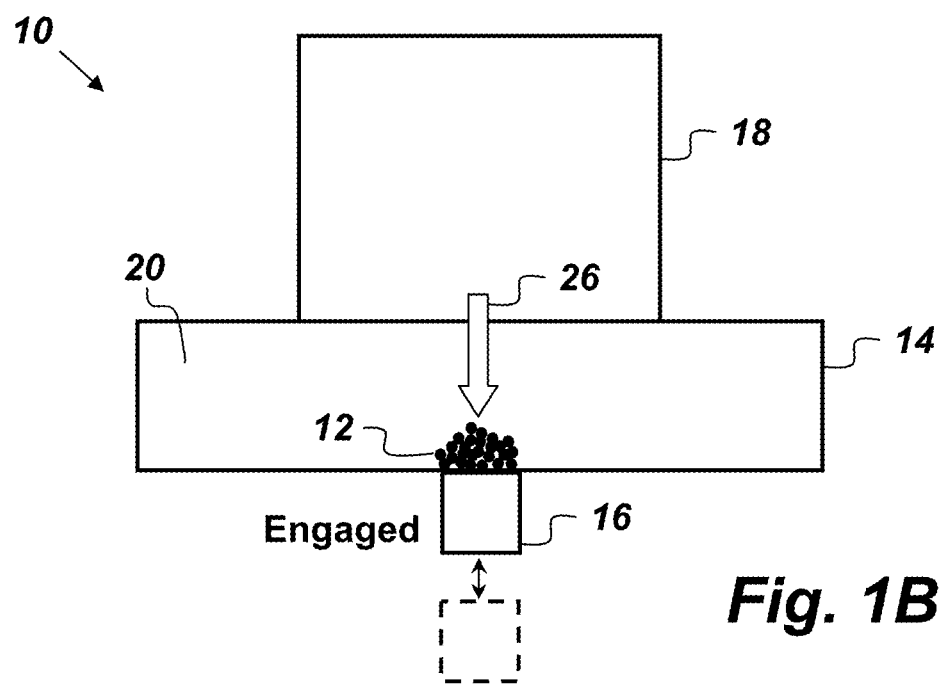

FIGS. 1A and 1B are illustrations of a perchlorate detector 10 that comprises, consists of, or consists essentially of capture matrices 12, a detection chamber 14, a selectively engageable magnet assembly 16, and a Raman spectrometer 18. The detector 10 is capable of extracting and detecting trace amounts of perchlorate (i.e., at or below 100 ppb) in a sample solution 20 using surface-enhanced Raman Spectroscopy (SERS). The detector 10 does not require the use of reagents, and does not suffer from interferences. The capture matrices 12 are SERS-active, magnetic, microparticles that are selective for perchlorate. The capture matrices 12 are designed to be added to the sample solution 20 to create a mixed suspension 22. The detection chamber 14 is configured to hold the sample solution 20 and the capture matrices 12. The magnet assembly 16 is coupled to the detection chamber 14 and is selectively engageable such that when the magnet assembly 16 is engaged or disengaged the capture matrices 12 are respectively confined or not confined to a confinement region 24 of the detection chamber 14. FIG. 1A shows the magnet assembly disengaged and FIG. 1B shows the magnet assembly engaged. The Raman spectrometer 18 is optically aligned (represented by the arrow 26) with the confinement region 24 of the detection chamber 14 and is configured to interrogate the capture matrices 12 when the magnet assembly 16 is engaged (see FIG. 1B) in order to detect and determine a concentration of perchlorate bound to the capture matrices 12.

Figure 2A:
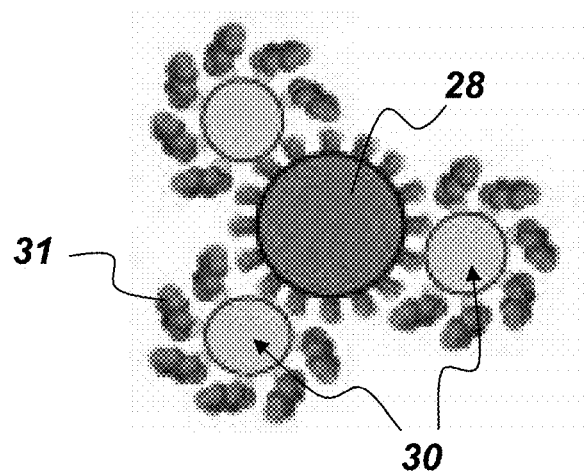
FIG. 2A is a schematic of a SERS-active capture matrix.
Figure 2B:
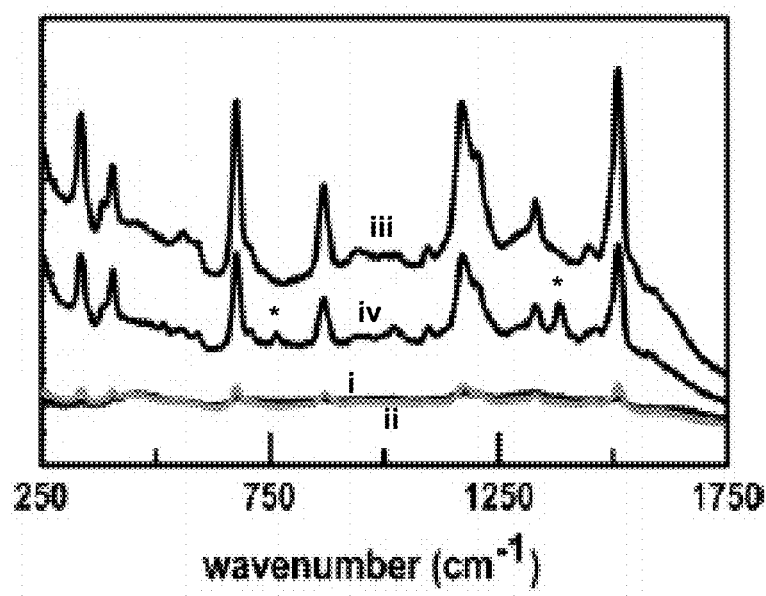
FIG. 2B is a plot of several SERS spectra.

FIG. 2A is a schematic of a SERS-active capture matrix. The capture matrices 12 may be any SERS-active, magnetic, microparticles that are selective for perchlorate. SERS-active capture matrices may be used for the trace detection of chemical species. Amine-derivatized magnetic microparticles 28 may be used to immobilize either Ag or Au colloidal nanoparticles 30. Afterwards the surface of the Ag/Au nanoparticles may be reacted with a thiol (R-SH) to form a self-assembled monolayer (SAM) 31. The R group of the thiol may be chosen to bind to a chemical species. Examples of SERS spectra obtained for pentachlorothiophenol (PCTP)-derivatized Au capture matrices in the presence and absence of naphthalene are shown in FIG. 2B. In FIG. 2B, i and ii are spectra obtained with the capture matrices suspended in solution and iii and iv are spectra obtained by concentrating the capture matrices on an optical surface. Naphthalene peaks are indicated by an asterisk (*). In i and ii, peaks due to the PCTP SAM can be discerned; however, they are very weak. Spectra iii and iv were obtained by using a neodymium iron boron (NdFeB) magnet to concentrate the capture matrices onto an optical surface. Once concentrated onto an optical surface, the SERS spectra exhibit highly resolved, intense peaks. As shown in iv, peaks due to naphthalene (indicated by *) can be seen indicating that the naphthalene partitioned into the PCTP coating. A suitable example of the capture matrices 12 selective for perchlorate include, but are not limited to, 2-dimethylaminoethanethiol hydrochloride (DMA) derivatized silver nanoparticles immobilized on magnetic microparticles.

Figure 3:
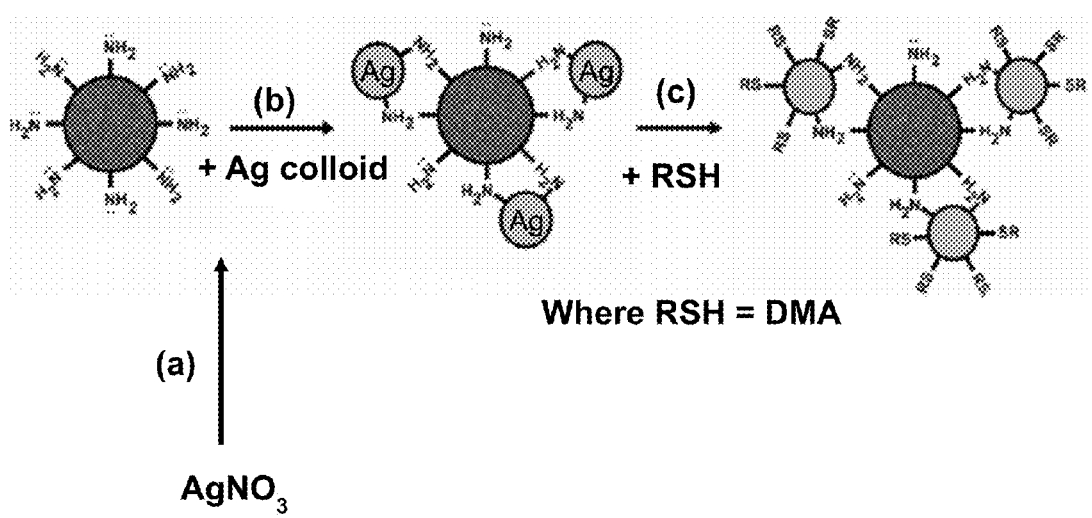
FIG. 3 is a pictorial representation of an example procedure that may be used to synthesize Ag/DMA capture matrices.

FIG. 3 is a pictorial representation of an example procedure that may be used to synthesize Ag/DMA capture matrices. The first step (a) is to synthesize colloidal Ag nanoparticles. In one example synthesis, a 500 mL aqueous solution containing 90 mg silver nitrate is placed in a 1000-mL round-bottom flask equipped with a condenser. The solution is brought to a vigorous boil while being stirred rapidly. Once the solution reaches a boil, 10 mL of 1% sodium citrate is added. Within 1 min, the color of the solution changes from clear to yellow. After refluxing for 1 hr, the solution is gray. The flask is removed from the heat and allowed to cool to room temperature. The colloidal suspension is then concentrated, by centrifugation, to a final volume of ~3 mL. In the second step (b), amine-derivatized magnetic microparticles are mixed with the Ag colloidal particles. The amine groups of the magnetic microparticles bind to the Ag colloidal nanoparticles to make SERS-active capture matrices. Once the surfaces of the magnetic microparticles are saturated with Ag nanoparticles, the SERS-active capture matrices are washed in ethanol. In the third step (c), An ethanolic solution of DMA is added to the SERS-active capture matrices. The thiol group of DMA binds to the Ag surface to form a SAM. It should be noted that Au nanoparticles can also be used to make SERS-active capture matrices specific for perchlorate.

Figure 4A:
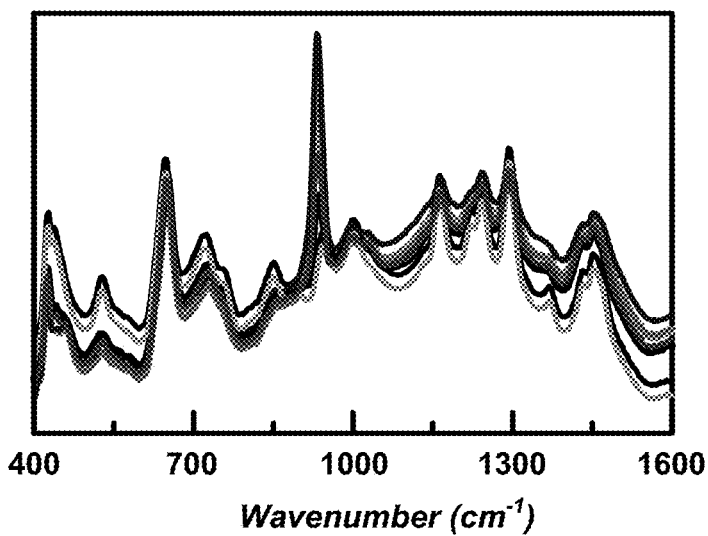
FIGS. 4A-4C are plots of experimental results regarding a conventional Ag/DMA SERS substrate.
Figure 4B:
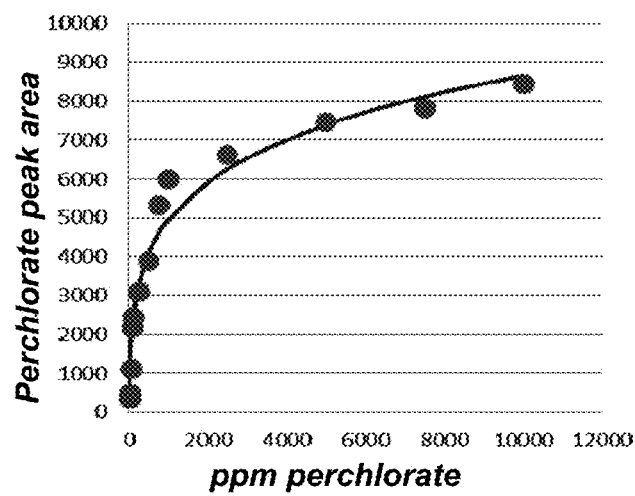
Figure 4C:
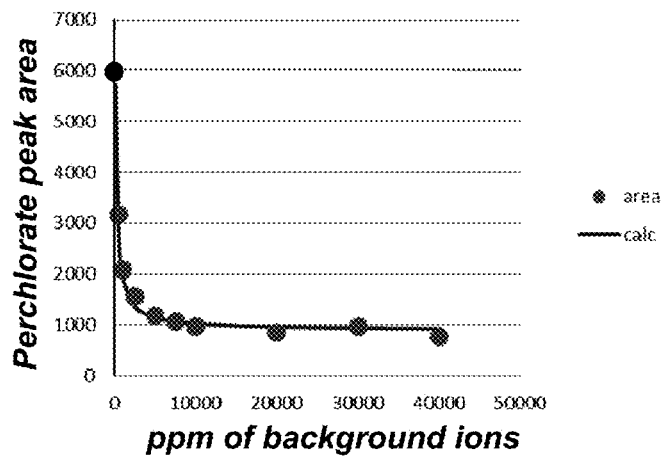

FIG. 4A shows spectra obtained for a Ag/DMA substrate as a function of perchlorate $ClO_4^-$ concentration in deionized water. The perchlorate peak in this embodiment occurs at 934 cm$^{-1}$. The calibration curve is shown in FIG. 4B. The DMA coating is highly selective for perchlorate. However, in the presence of two to five orders of magnitude higher concentrations of background ionic species, a decrease in perchlorate peak intensity is observed to occur. However, this can be corrected for if the concentration of the background ionic species is known. FIG. 4C is a plot of perchlorate peak area plotted as a function of ppm of background ion concentration where the circles are the experimental data and the line trace under the circles is the best fit line. This curve is described by the following equation:

$$A = A_0 - ((VC)/(K+C)) \quad (1)$$

where $A$ and $A_0$ are the perchlorate peak area in the presence and absence of background ions, respectively; $C$ is the concentration of background ions in ppm; and $V$ and $K$ are constants obtained through curve fitting. For this example, the values of $A_0$, $V$, and $K$ are 6000, 5100, and 250, respectively. Once the values of $A_0$, $V$, and $K$ are known, the corrected perchlorate peak area can be calculated. Once the corrected peak area is known, the concentration of perchlorate can be determined from the calibration curve obtained in the absence of background anionic species, FIG. 4B. As can be seen, a perchlorate peak area of 6000 a.u. (arbitrary units) translates to a perchlorate concentration of 1000 ppm.

The detection chamber 14 of the perchlorate detector 10 may be any container capable of holding the sample solution 20 and the capture matrices 12. A suitable example of the detection chamber 14 includes, but is not limited to, a small diameter, thin-walled, glass or quartz tube.

The magnet assembly 16 may be any device capable of subjecting the contents of the detection chamber 14 to a magnetic field having at least two field-strength levels that may be selectively engaged by the magnet assembly 16. A suitable example of the magnet assembly 16 includes, but is not limited to, an electromagnet positioned outside the detection chamber 14 such that when energized the electromagnet creates an electric field that attracts and confines the capture matrices 12 to the confinement region 24, and such that when de-energized, the electric field is diminished such that the capture matrices 12 are not confined to the confinement region 24. Another suitable example of the magnet assembly 16 is a permanent magnet mounted to a movable platform. In the permanent magnet embodiment, the movable platform may be moved close to the detection chamber 14 in order to attract and confine the capture matrices to the confinement region 24, and when then platform is moved away from the detection chamber 14 the capture matrices 12 are free to move about the suspension 22 (i.e., they are not confined to the confinement region 24).

The Raman spectrometer 18 may be any Raman spectrometer capable of interrogating the capture matrices 12 in the detection chamber 14. For example, the Raman spectrometer 18 may have a laser, dispersive element, and CCD array in one system. The Raman spectrometer 18 may be sized and equipped for portable/in-field operation. The sample solution 20 may be a sample of surface or groundwater. In addition, the sample solution 20 may also be an aqueous suspension of soil or sediment.

Figure 5A:
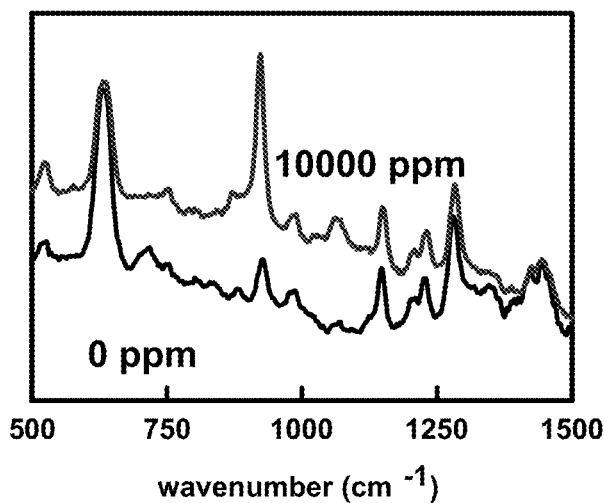
FIGS. 5A-5C show spectral data obtained using an embodiment of a perchlorate detector.
Figure 5B:
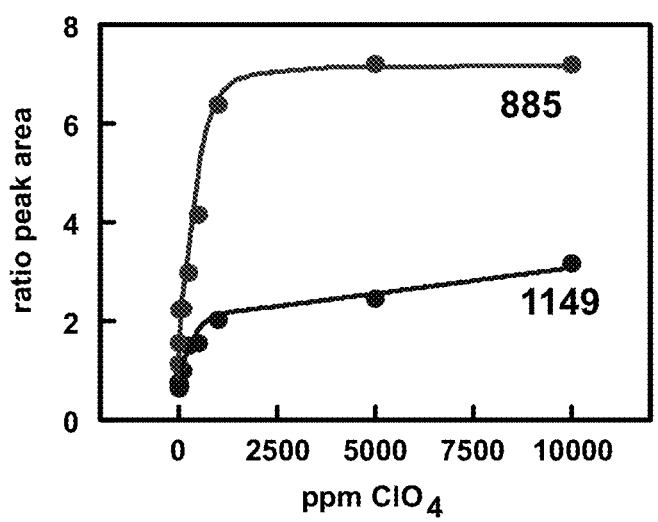
Figure 5C:
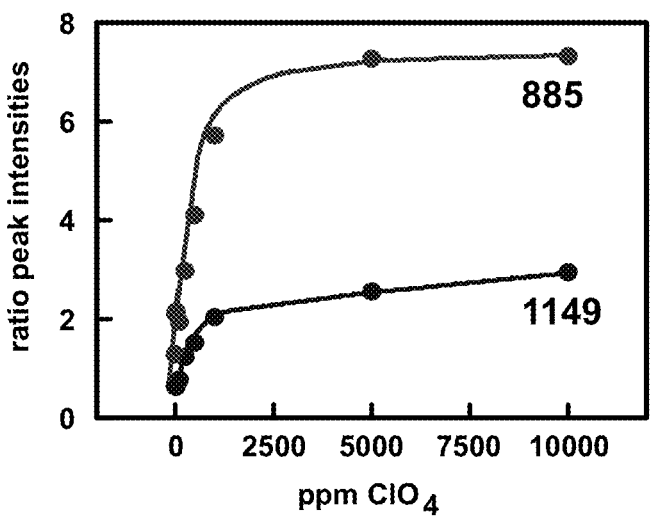

FIGS. 5A-5C show spectral data obtained using an embodiment of the perchlorate detector 10. FIG. 5A shows SERS spectra of Ag/DMA capture matrices in 0 and 10$^4$ ppm perchlorate. Peak area should not be used to generate a calibration curve for the capture matrices due to variability in the SERS peaks of the coating and the SERS continuum. To get around this problem, a calibration curve can be generated by ratioing the peak area/intensity of the perchlorate peak to the peak area/intensity of a DMA peak that does not change when perchlorate is added. FIG. 5B shows calibration curves generated by ratioing the perchlorate peak area to DMA peak areas. DMA peaks are at 885 and 1149 cm$^{-1}$. FIG. 5C shows calibration curves generated by ratioing the perchlorate peak intensity to DMA peak intensities. DMA peaks are at 885 and 1149 cm$^{-1}$. FIGS. 5B-5C show that reasonable calibration curves can be obtained by ratioing the peak areas/intensities and plotting those ratios as a function of perchlorate concentration.

Figure 6:
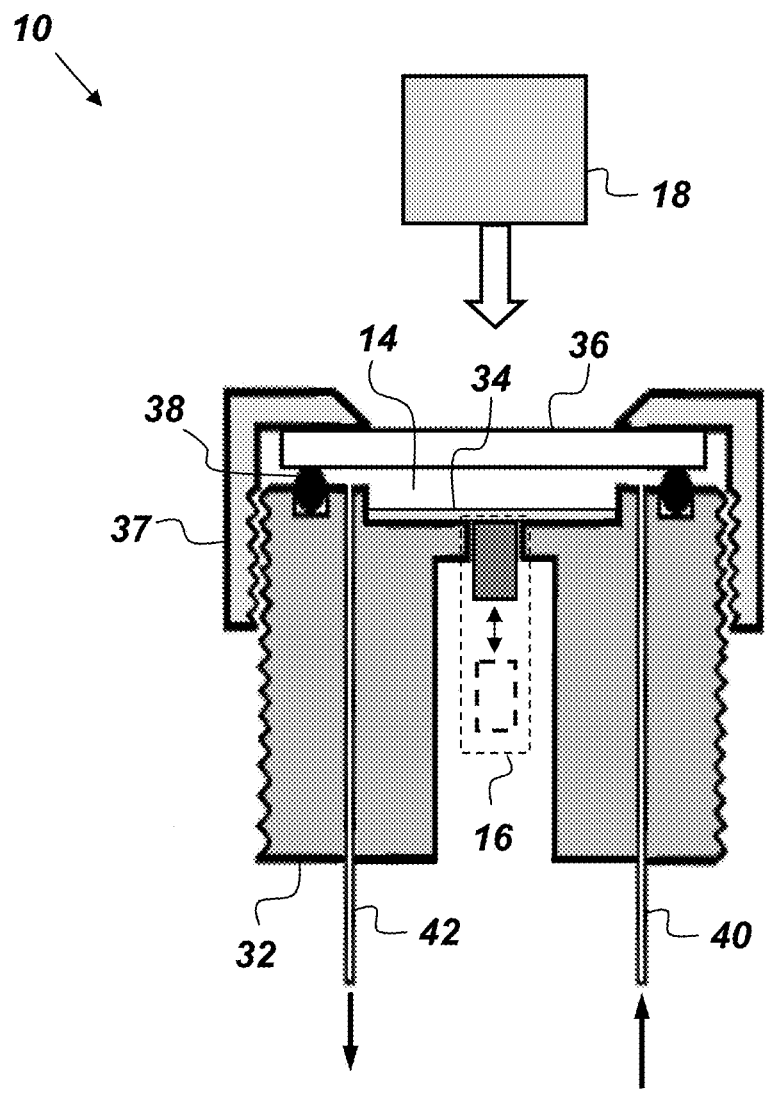
FIG. 6 is a cross-sectional, side view of an embodiment of a perchlorate detector.

FIG. 6 is a schematic of a prototype, flow-through cell embodiment of the perchlorate detector 10. In this embodiment, the detection chamber 14 is formed out of a Teflon® cell body 32. A chemically resistant epoxy (Epoxy Patch 1C, Hysol) was used to epoxy a 0.1 mm thick gold foil 34 on the inside surface of the cell. The magnet assembly 16 in this embodiment is mounted below the gold foil 34. A 25 mm diameter, 2 mm thick sapphire disk was used as an optically transparent window 36 into the detection chamber 14. A Kel-F® window retainer 37 holds the window 36 in place. An O-ring 38 provides a leak-tight seal between the window 36 and the cell body 32. The inlet 40 and outlet 42 consist of 20 gauge stainless steel tubes that have been epoxied in place using a chemically resistant epoxy (Epoxy Patch 1C, Hysol®). The distance between the surface of the magnet assembly 16 and the gold covered sample surface is ~0.1 mm. When the magnet assembly 16 was engaged, the pull force was found to be sufficient to hold the capture matrices 12 in place when perchlorate solution was flowed through the cell. For SERS measurements, the flow-through cell was held in place below the point and shoot optics of the spectrometer 18 with the "Opti-Claw" optical mount (New Focus, part no. 9832) mounted on an x,y,z-translation stage (Newport Corporation, part no. 460A).

Figure 7:
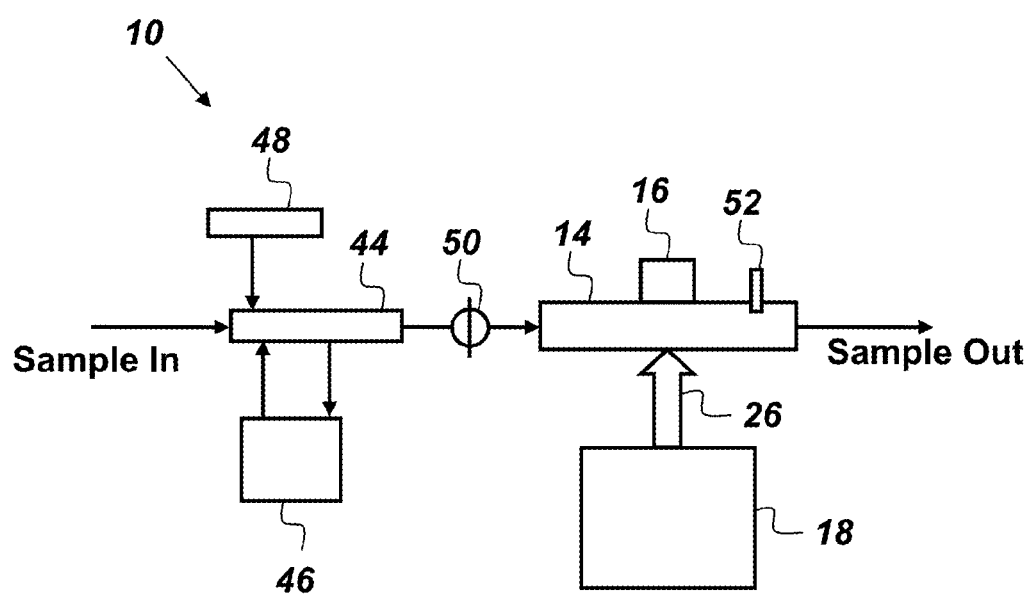
FIG. 7 is an illustration of an embodiment of a perchlorate detector.
Figure 10:
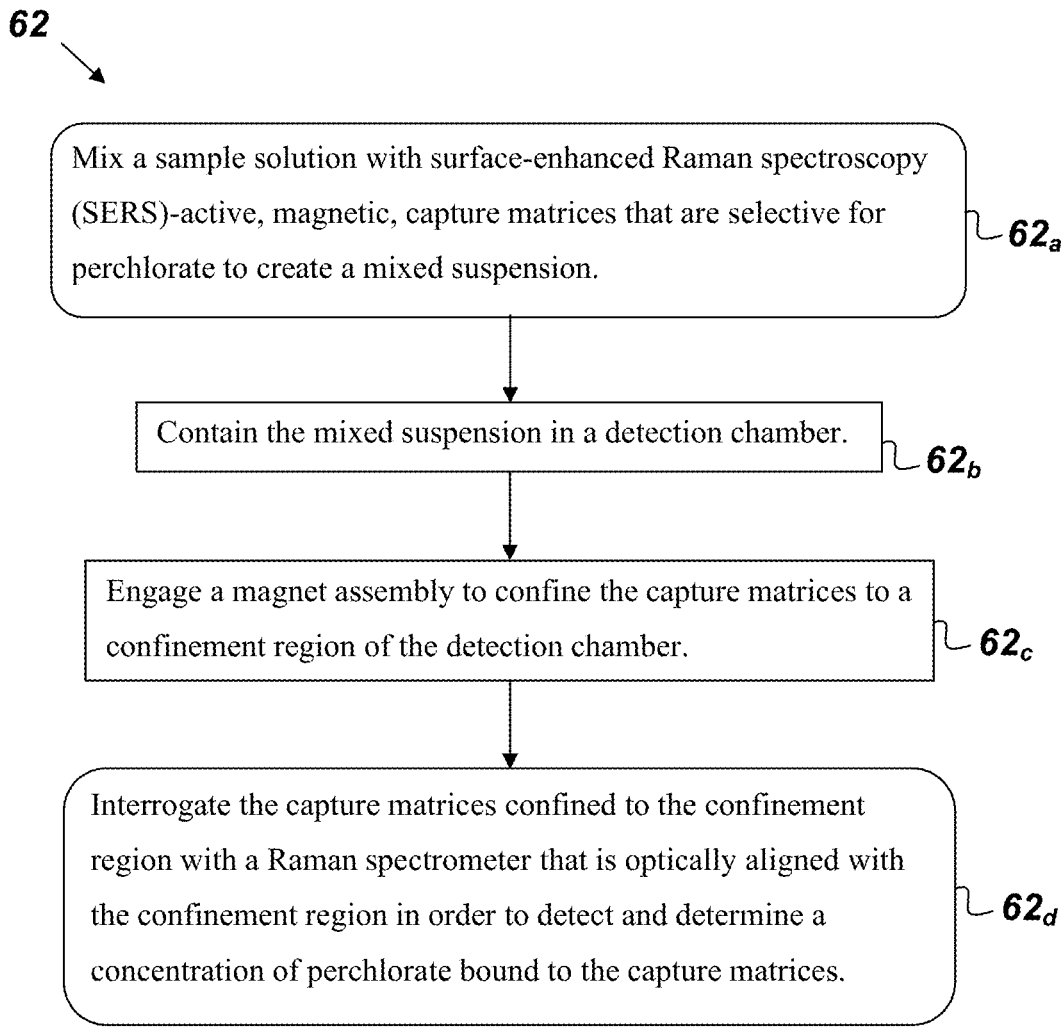
FIG. 10 is a flowchart.

FIG. 7 is an illustration of an embodiment of the perchlorate detector 10 further comprising, consisting of, or consisting essentially of a mixer 44 that is operatively coupled to the detection chamber 14. The mixer 44 is configured to mix the capture matrices 12 and the sample solution 20 so as to increase interaction between the sample solution 20 and the capture matrices 12 to increase capture efficiency and to lower detection limits. Suitable examples of the mixer 44 include, but are not limited to an in-line folded flow mixer, an agitator, a nonmagnetic stirring rod, and a vortex mixer. The embodiment of the mixer 44 shown in FIG. 10 includes a pump 46 and a reservoir 48 of capture matrices 12. The mixer 44 may be connected to the detection chamber 14 via a valve 50. Also shown in FIG. 10 is an optional conductivity meter 52 that is operatively coupled to the detection chamber 14 and configured to measure the conductivity of the sample solution 20. The conductivity is directly proportional to the concentration of background ions present in the sample. This concentration is then used in equation (1) to obtain the corrected perchlorate peak area/intensity. The mixer 44 may be relatively large to enable detection limits of perchlorate in the low ppb range.

Figure 8:
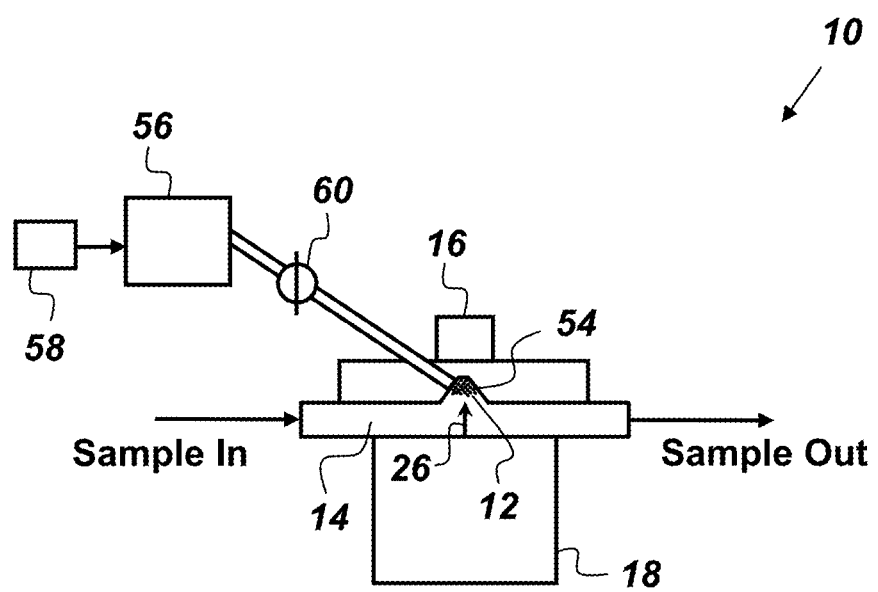
FIG. 8 is an illustration of an embodiment of a perchlorate detector.

FIG. 8 is a cross-sectional side view of an embodiment of the perchlorate detector 10 wherein the detection chamber 14 further comprises an indentation 54 at the confinement region 24. Experiments showed that confining the capture matrices inside conical wells increased signal intensity. The indentation 54 may be any desired size and shape. Suitable shapes for the indentation 54 include, but are not limited to spherical, ovoid, and conical. In the embodiment shown in FIG. 8, the indentation 24 has a conical shape. This embodiment also comprises a water reservoir 56, a pump 58, and a valve 60. When the magnet assembly 16 is engaged, the capture matrices 12 are confined to the confinement region 24, which in this embodiment, corresponds to the indentation 54, such as is shown in FIG. 8. When the magnet assembly 16 is disengaged, the valve 60 may be opened to allow water from the water reservoir 56 to flush out the indentation 54. After the capture matrices 12 have been interrogated by the Raman spectrometer 18, the suspension 22 may be flushed out of the detection chamber 14 such that the capture matrices 12 may be collected for verification by further testing. The perchlorate detector 10's ability to quickly move a suspension 22 into the detection chamber 14, interrogate the capture matrices 12 and then flush out the suspension 22 allows for multiple sample solutions 20 to be tested in rapid succession.

Figure 9A:
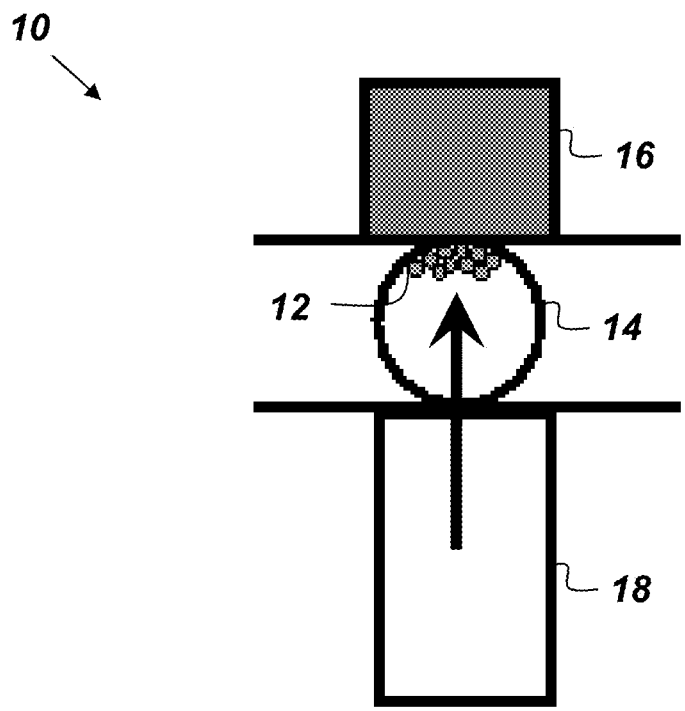
FIGS. 9A and 9B are cross-sectional, front view illustrations of embodiment of a perchlorate detector.
Figure 9B:
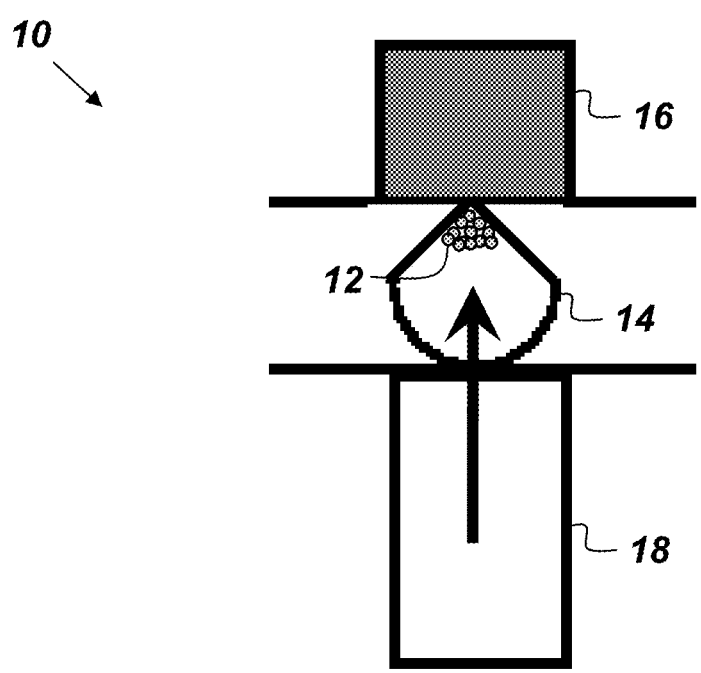

FIGS. 9A and 9B are cross-sectional end views of different embodiments of the detection chamber 14. The detection chamber 14 may have any desired size and shape. In FIG. 9A, the detection chamber 14 has a circular cross section. In FIG. 9B, the detection chamber 14 has a v-shaped channel. It may be desirable to limit the size of the detection chamber 14 in order to reduce the optical path between the Raman spectrometer 18 and the capture matrices 12.

FIG. 10 is a flowchart of a method 62 for using the perchlorate detector 10. The first step $62_a$ provides for mixing the sample solution 20 with the capture matrices 12 that are selective for perchlorate to create the mixed suspension 22. The next step $62_b$ provides for containing the mixed suspension 22 in the detection chamber 14. The next step $62_c$ provides for engaging the magnet assembly 16 to confine the capture matrices 12 to the confinement region 24 of the detection chamber 14. The next step $62_d$ provides for interrogating the capture matrices 12 confined to the confinement region 24 with the Raman spectrometer 18 that is optically aligned with the confinement region 24 in order to detect and determine a concentration of perchlorate bound to the capture matrices 12. The method 62 may optionally further comprise the step of testing the mixed suspension 22 for chloride ions. In an embodiment of the perchlorate detector 10, the step of testing the mixed suspension 22 for chloride ions may comprise measuring a conductivity of the mixed suspension 22 and estimating a concentration of chloride ions in the mixed suspension 22 based on the measured conductivity. The perchlorate peak area may be corrected in light of the estimated concentration of chloride ions in the mixed suspension 22 according to Equation 1. Alternatively, solid phase extraction may be used to remove chloride ions from the sample solution 20 before the sample solution 20 is mixed with the capture matrices 12. The remaining concentration of chloride may then be measured using a chloride ion selective electrode after the sample solution 20 and capture matrices 12 are mixed. The method 62 may be performed without using reagents. In other words, the perchlorate detector 10 may be used to detect trace amounts of perchlorate without the use of reagents, preconcentration of the analyte, and/or frequent recalibration of the instrument.

From the above description of the perchlorate detector 10, it is manifest that various techniques may be used for implementing the concepts of the detector 10 without departing from the scope of the claims. The described embodiments are to be considered in all respects as illustrative and not restrictive. The method/apparatus disclosed herein may be practiced in the absence of any element that is not specifically claimed and/or disclosed herein. It should also be understood that the perchlorate detector 10 is not limited to the particular embodiments described herein, but is capable of many embodiments without departing from the scope of the claims.

We claim:

1. A perchlorate detector comprising:
    surface-enhanced Raman spectroscopy (SERS)-active, magnetic, capture matrices that are selective for perchlorate, wherein the capture matrices are designed to be added to a sample solution;
    a detection chamber configured to hold the sample solution and the capture matrices wherein the detection chamber comprises a confinement region having an indentation;

a selectively engageable magnet assembly coupled to the detection chamber such that when the magnet assembly is engaged or disengaged the capture matrices are respectively confined or not confined to the confinement region of the detection chamber;

a Raman spectrometer optically aligned with the confinement region of the detection chamber and configured to interrogate the capture matrices when the magnet assembly is engaged in order to detect and determine a concentration of perchlorate bound to the capture matrices; and a water reservoir hydraulically coupled to the indentation via a valve such that when the valve is open and the magnetic assembly is disengaged water enters the indentation and flushes the capture matrices out of the indentation.

2. The perchlorate detector of claim 1, further comprising a mixer operatively coupled to the detection chamber and configured to mix the capture matrices and the sample solution so as to increase interaction between the sample solution and the capture matrices to increase capture efficiency.

3. The perchlorate detector of claim 2, wherein the mixer is an agitator.

4. The perchlorate detector of claim 2, wherein the mixer is a vortex mixer.

5. The perchlorate detector of claim 2, wherein the mixer is a folded flow inline mixer.

6. The perchlorate detector of claim 2, further comprising a conductivity meter operatively coupled to the detection chamber and configured to measure a conductivity of the sample solution.

7. The perchlorate detector of claim 1, wherein the capture matrices are Ag/2-dimethylaminoethanethiol hydrochloride (DMA) nanoparticles immobilized on amine- or thiol-derivatized magnetic microparticles.

8. The perchlorate detector of claim 1, wherein the indentation has a shape that is selected from the group consisting of conical, ovoid, and spherical.

9. The perchlorate detector of claim 1, wherein the detection chamber is a v-shaped channel.

10. The perchlorate detector of claim 1, wherein the detection chamber is a tube having a round cross-section.

11. A perchlorate detection method comprising the following steps:

mixing a sample solution with surface-enhanced Raman spectroscopy (SERS)-active, magnetic, capture matrices that are selective for perchlorate to create a mixed suspension;

containing the mixed suspension in a detection chamber;

engaging a magnet assembly to confine the capture matrices to a confinement region of the detection chamber;

interrogating the capture matrices confined to the confinement region with a Raman spectrometer that is optically aligned with the confinement region in order to detect and determine a concentration of perchlorate bound to the capture matrices; and disengaging the magnet assembly and opening a valve to allow water from a water reservoir that is hydraulically coupled to the confinement region to flush the capture matrices out of the confinement region.

12. The method of claim 11, further comprising the step of testing the mixed suspension for chloride ions.

13. The method of claim 12, wherein the step of testing the mixed suspension for chloride ions comprises measuring a conductivity of the mixed suspension and estimating a concentration of chloride ions in the mixed suspension based on the measured conductivity.

14. The method of claim 13, further comprising the step of correcting a perchlorate peak area in light of the estimated concentration of chloride ions in the mixed suspension.

15. The method of claim 14, wherein the step of correcting the perchlorate peak area is performed according to the following equation: $A=A0-((VC)/(K+C))$, where A and A0 are respectively the perchlorate peak area in the presence and absence of background ions, C is the concentration of background chloride ions in ppm; and V and K are constants obtained through curve fitting.

16. The method of claim 12, further comprising the steps of:

using solid phase extraction to remove chloride ions from the sample solution before the sample solution is mixed with the capture matrices; and measuring a remaining concentration of chloride using a chloride ion selective electrode after the sample solution and capture matrices are mixed.

17. The method of claim 11, further comprising the step of collecting the capture matrices for verification after they have been interrogated.

18. The method of claim 11, wherein the steps are performed without using reagents.

* * * * *